United States Patent [19]

Estis

[11] Patent Number: 4,499,014

[45] Date of Patent: Feb. 12, 1985

[54] METHOD FOR PURIFYING GAMMA-INTERFERON

[75] Inventor: Leonard F. Estis, North Brunswick, N.J.

[73] Assignee: Interferon Sciences, Inc., New York, N.Y.

[21] Appl. No.: 577,908

[22] Filed: Feb. 7, 1984

[51] Int. Cl.³ .................. A61K 45/02; C07G 7/00
[52] U.S. Cl. ................... 260/112 R; 424/85; 435/68; 435/272; 435/811; 436/548
[58] Field of Search ............ 260/112 R; 424/85; 435/68, 172, 272, 811; 436/548

[56] References Cited

U.S. PATENT DOCUMENTS

| | | | |
|---|---|---|---|
| 4,017,600 | 4/1977 | Stewart et al. | 424/85 |
| 4,172,071 | 10/1979 | De Maeyer et al. | 260/112 R |
| 4,273,703 | 6/1981 | Osther et al. | 260/112 R |
| 4,289,689 | 9/1981 | Friesen et al. | 260/112 R |
| 4,289,690 | 9/1981 | Pestka et al. | 260/112 R |
| 4,296,025 | 10/1981 | Sugimoto | 260/112 R |
| 4,314,935 | 2/1982 | Uemura et al. | 260/112 R |
| 4,359,389 | 11/1982 | Heine | 424/85 X |
| 4,432,895 | 2/1984 | Tarnowski | 260/112 R |
| 4,440,675 | 4/1984 | Braude | 260/112 R |

OTHER PUBLICATIONS

Nature, 271, 622–625, (1978), De Maeyer et al.
Proc. Natl. Acad. Sci., U.S.A., 78, 1601–1605, (1981), Yip et al.
Proc. Natl. Acad. Sci., U.S.A., 79, 1820–1824, (1982), Yip et al.
Mol. Immunol., 17, 625–633, (1980), Wiranowska-Stewart et al.

Primary Examiner—Howard E. Schain
Attorney, Agent, or Firm—Vincent P. Pirri; Maurice M. Klee

[57] ABSTRACT

A method is provided for restoring some or all of the activity of gamma-interferon which has been in contact with an acidic solution comprising the steps of: (a) placing the gamma-interferon in a solution which has a pH between about 5.5 and 9.5; and (b) incubating the solution at a temperature of between about 2° C. and 8° C. for a period of at least 24 hours. The method allows antibody affinity chromatography employing acid elution to be used to purify gamma-interferon, in that, the activity of the acid-eluted gamma-interferon can be essentially completely restored using the reactivation process.

13 Claims, 10 Drawing Figures

WESTERN BLOT ANALYSIS OF POLYCLONAL
ANTIBODY AFFINITY PURIFIED GAMMA INTERFERON

WESTERN BLOT ANALYSIS OF MONOCLONAL
ANTIBODY AFFINITY PURIFIED GAMMA INTERFERON

METHOD FOR PURIFYING GAMMA-INTERFERON

BACKGROUND OF THE INVENTION

1. Field of the Invention

This invention relates to gamma-interferon and in particular to a method for purifying gamma-interferon using monoclonal and polyclonal antibodies.

2. Description of the Prior Art

Immune or gamma-interferon was originally classified on a physical basis as Type II Interferon due to its lability to acid treatment and/or heating to 56° C. This operational classification distinguished it from virus-induced or Type I Interferons (alpha and beta) which, in general, are not acid or heat labile. As a result of the widespread availability of specific antisera against each of the major interferon classes (alpha, beta, and gamma), classification and distinction of each type is now usually made by serological or immunological methods. Despite this, gamma-interferon preparations are still identified as such by their rapid inactivation upon acid treatment. See, *The Interferon System*, 2nd edition, W. E. Stewart II, Springer-Verlag, New York, 1981.

In general, the acid inactivation process employed to identify gamma-interferon has involved reduction of the pH of a gamma-interferon containing solution to about 2, a short incubation at this pH (a few minutes to several hours), and then addition of base or dialysis against PBS to bring the pH to neutrality. Activity recoveries after such treatment are usually about 10% of control activity. To the present inventor's knowledge, there have been no reports to date showing recovery of gamma-interferon's antiviral activity to levels significantly above 10% after acid treatment.

One of the powerful tools which has been used to obtain purified solutions of selected biological materials is antibody affinity chromatography. In accordance with this technique, a chromatography column containing covalently immobilized antibodies to the biological material to be purified is prepared, and a solution containing the material, along with contaminants, is passed through the column. The immobilized antibodies form antigen-antibody complexes with the selected material which remain on the column, while the rest of the solution, including, in general, most of the contaminants, passes through the column. To free the selected biological material from the immobilized antibodies, a second solution, capable of disassociating the antigen-antibody complexes, is passed through the column. Although a variety of materials (e.g., potassium thiocyanate, urea, guanidine hydrochloride, and the like) can be included in the second solution so as to achieve the desired disassociation, the most commonly used approach is to simply make the solution acidic.

Prior to the present invention, because of gamma-interferon's known susceptibility to acid deactivation, antibody affinity chromatography has not been used to purify this important biological material. That is, although antibodies to gamma-interferon which can be immobilized on a chromatography column have been available, the art has not used affinity chromatography with gamma-interferon because there was no known way of eluting this interferon from an antibody column without destroying most of its biological activity. Acid elution, the standard elution technique, was hardly a viable approach in view of the fact that one of the basic assays for gamma-interferon involves testing for inactivation in the presence of acid. Moreover, many of the other known materials capable of producing disassociation of antigen-antibody complexes, e.g., potassium thiocyanate and urea, had also been found to inactivate gamma-interferon.

Rather than using affinity chromatography, the art turned to complicated, multi-step purification schemes. For example, European Patent Publication No. 63,482 reports a four step purification technique run at neutral or basic pHs which includes passing a gamma-interferon containing solution through a controlled pore glass bead column, a concanavalin A-Sepharose or lentil lectin-Sepharose or pea lectin-Sepharose column, a heparin-Sepharose or procian red-Sepharose column, and a gel-filtration column. Similarly, Yip, Y. K., Barrowclough, B. S., Urban, C., and Vilcek, J., *Proc. Natl. Acad. Sci.* (USA), Vol. 79, pp. 1820–1824, March 1982, report a three step purification process for gamma-interferon involving a first adsorption and elution from controlled-pore glass and a second adsorption and elution from concanavalin A-Sepharose, followed by adsorptive removal of contaminating proteins on DEAE-Sephacel at pH 8.0.

SUMMARY OF THE INVENTION

In view of this state of the art, it is an object of this invention to provide an improved method for purifying gamma-interferon. More particularly, it is an object of the invention to provide a method for purifying gamma-interferon which employs antibody affinity chromatography. It is a further object of the invention to provide such an affinity chromatography technique wherein the gamma-interferon is stripped from an antibody column by acid elution. It is an additional object of the invention to provide a method for reactivating acid-inactivated gamma-interferon.

To achieve these and other objects, it has been found, in accordance with one aspect of the invention, that although acidic conditions do inactivate gamma-interferon, the interferon can be reactivated by being incubated for an extended period of time at a controlled pH and temperature. More particularly, it has been found that acid inactivated gamma-interferon will regain a substantial fraction of its original biological activity if it is held at a pH of between about 5.5 and 9.5 and at a temperature of between about 2° C. and 8° C. for a period of at least 24 hours. In certain preferred embodiments of the invention, the reactivation process is carried out at a pH between about 6.0 and 9.0, at a temperature of about 4° C., and for a period of about 96 hours.

By means of this reactivation process, for the first time, the invention allows for the use of antibody affinity chromatography in the purification of gamma-interferon. Specifically, in accordance with this aspect of the invention, a method for purifying gamma-interferon is provided which comprises the steps of:

(a) preparing one or more antibodies to gamma-interferon;

(b) immobilizing the one or more antibodies on a solid support;

(c) contacting a first solution containing gamma-interferon with the one or more immobilized antibodies so as to form immobilized antibody-antigen complexes between the gamma-interferon and the one or more immobilized antibodies;

(d) separating the first solution from the immobilized antibody-antigen complexes;

(e) contacting the immobilized antibody-antigen complexes with a second solution having an acidic pH so as to disassociate the gamma-interferon form the one or more immobilized antibodies and into the second solution, the acidity of said second solution having the effect of partially or completely deactivating the disassociated gamma-interferon;

(f) separating the second solution from the one or more immobilized antibodies; and (g) restoring some or all of the activity of the gamma-interferon in the second solution by adjusting the pH of that solution to between about 5.5 and 9.5 and then incubating the pH adjusted solution at a temperature of between about 2° C. and 8° C. for a period of at least 24 hours. In certain preferred embodiments of the purification process, the reactivation is conducted at a pH between about 6.0 and 9.0, at a temperature of about 4° C., and for a period of about 96 hours.

BRIEF DESCRIPTION OF THE DRAWING

In FIG. 5, the titer of the acidified, pH adjusted sample expressed as a percent of control is shown. In FIG. 6, the absolute titers of the acidified (o) and control (x) samples are shown.

FIG. 7 shows the activity of the HCl-acidified, pH adjusted sample expressed as a percent of control. FIG. 8 shows the absolute titers of the acidified (o) and control (x) samples.

DESCRIPTION OF THE PREFERRED EMBODIMENTS

Figure 1:
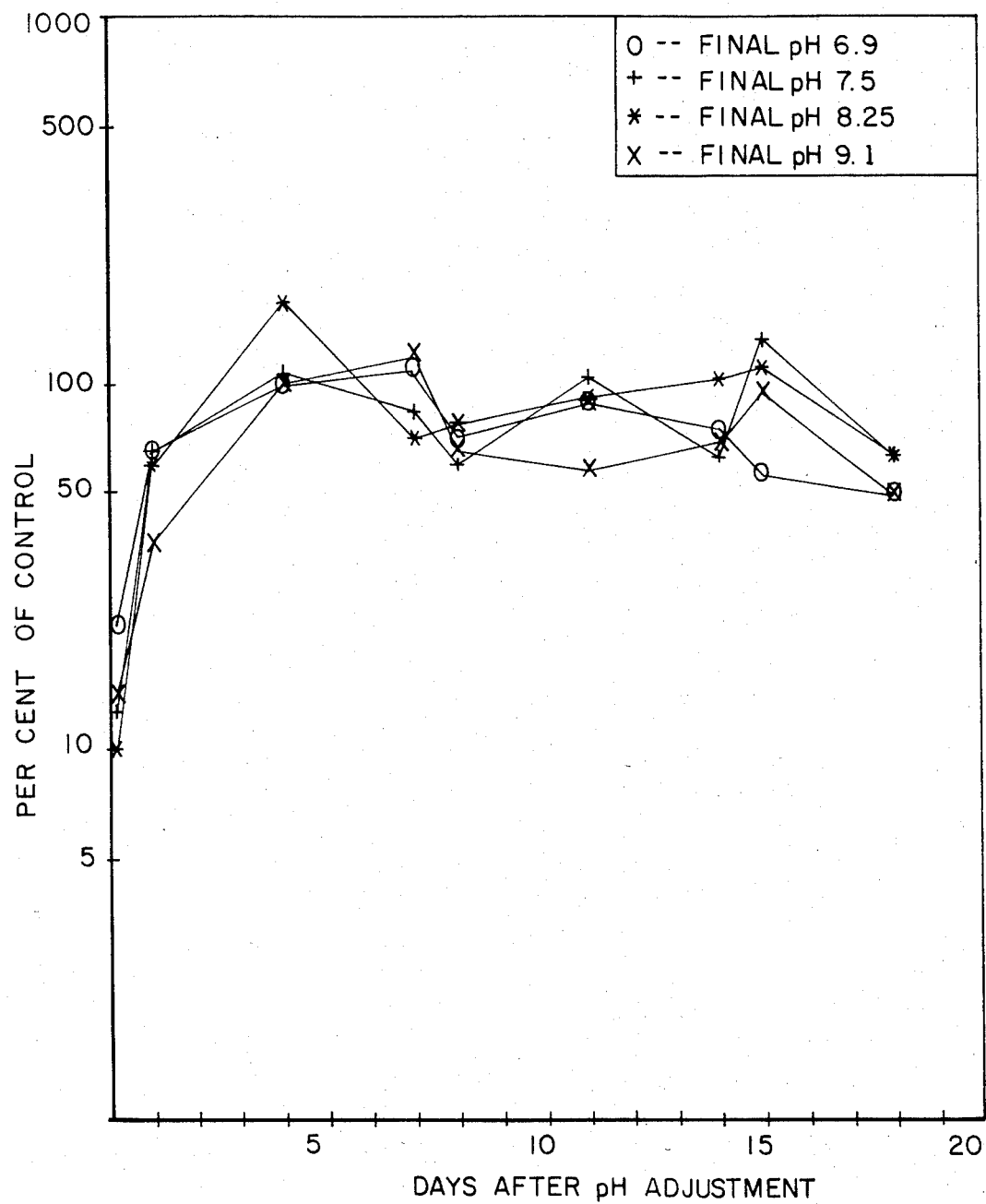
FIG. 1 is a graph showing reactivation of human gamma-interferon incubated at pH 2.4 for 1 hour. More particularly, partially purified human gamma-interferon (specific activity $2 \times 10^4$ u/mg) was diluted 1:100 in citric acid buffer (final pH=2.4) and incubated on ice for 60 minutes. 10 ml aliquots were pH-adjusted using: NaOH to pH 6.9 (o); solid TRIS to pH 7.5 (+); solid TRIS to pH 8.25 (*); and solid TRIS to pH 9.1 (x). The control for this experiment was a 1:100 dilution of the same interferon into standard assay media, pH 7.2. The control was incubated on ice at 4° C. in exactly the same manner as the acidified and pH adjusted solutions. Day 0 samples were assayed 2 hours after pH adjustment with base.

As described above, the present invention relates to a method for reactivating acid-inactivated gamma-interferon and to the use of that method in the purification of gamma-interferon by antibody affinity chromatography.

The reactivation method comprises the steps of: (a) placing the gamma-interferon in a solution which has a pH between about 5.5 and 9.5; and (b) incubating the solution at a temperature of between about 2° C. and 8° C. for a period of at least 24 hours. Preferably, the solution should have a pH of between about 6.0 and 9.0, and the temperature should be about 4° C. Although incubation periods as short as 4 hours will serve to restore a significant fraction of the gamma-interferon's activity, periods on the order of about 24 to 96 hours are preferred, and a period on the order of 96 hours, most preferred. Besides having a pH of between 5.5 and 9.5, it is considered desirable, but not necessary, for the reactivation solution to have a moderate ionic strength, e.g., on the order of about 0.1 to 0.5, and a moderate protein concentration, e.g., on the order of about 0.05 mg/ml to 2.0 mg/ml.

The affinity chromatography procedure includes the following steps: (a) preparation of one or more antibodies to gamma-interferon; (b) immobilization of those antibodies on a solid support in the form of a chromatography column; (c) passing a gamma-interferon containing solution through the column; (d) eluting the gamma-interferon from the column with acid; and (e) reactivating the gamma-interferon using the reactivation procedure.

The antibodies to gamma-interferon can be prepared in a number of ways known to the art. For example, polyclonal antibodies can be prepared by the methods described in Benedict, A. A., et al., "Production of Antiserum", *Methods in Immunology,* 1:197–306 (1967), and monoclonal antibodies can be prepared by the methods described in Section 1 of Volume 92 of *Methods in Enzymology,* (1983). In general, because of their specificity, monoclonal antibodies are preferred for use with the present invention. A particularly preferred method for producing a monoclonal antibody to gamma-interferon is described below in Example 3.

Once the antibodies have been obtained, they can be covalently linked to solid supports in a number of ways well known to the art. For example, immobilization can be on cyanogen bromide activated Sepharose 4B (Pharmacia, Piscataway, NJ), Trisacryl (LKB, Bethesda, MD), or similar materials. Covalent attachment of the antibodies to these supports is described in the product brochures supplied by the manufactures of these products. For example, attachment to cyanogen bromide activated Sepharose 4B simply involves overnight incubation of the antibodies with the solid support in a 0.5M sodium carbonate buffer (pH 8.0). Because of its wide use to date, cyanogen bromide activated Sepharose 4B is considered a particularly preferred support for use with the present invention.

The gamma-interferon to be purified can be produced by various procedures. One suitable procedure is described by Johnson et al in *Methods in Enzymology, Vol. 78*, pages 158-162 (1981). Another method appears in European Patent Publication No. 63,482, referred to above. A particularly preferred method for producing gamma-interferon is described in U.S. patent application Ser. No. 446,160, filed on Dec. 2, 1982, and assigned to the same assignee as the present invention.

Because antibody affinity chromatography is capable of purifying gamma-interferon without the aid of other purification procedures, the gamma-interferon containing solution which is applied to the column is preferably in crude form. To reduce the load volume applied to the column, the crude gamma-interferon is preferably concentrated, e.g., $100\times$, using, for example, a hollow fiber filter. Of course, if desired, the gamma-interferon containing solution can be partially purified prior to application to the column by techniques such as adsorption to controlled-pore glass beads or silicic acid beads, and/or ion-exchange chromatography on DEAE-Sephacel or similar materials.

The acid solution used to elute the bound gamma-interferon from either a polyclonal or monoclonal antibody column can have various pHs and compositions. Examples of suitable eluting solutions include 0.1M citric acid, pH 2.0, 1M propionic acid, pH 2.5, and 0.1M glycine, pH 3.0.

Without intending to limit it in any manner, the present invention will be more fully described by the following examples.

EXAMPLE 1

Reactivation of Acid Inactivated Gamma-Interferon Methods and Materials

1. Gamma-Interferon Production

Gamma-interferon was prepared following the method described in U.S. patent application Ser. No. 446,160, referred to above. Briefly, pooled human buffy coats from healthy human donors (Red Cross, Philadelphia, Pa.) were prepared for induction by centrifugation and subsequent removal of most of the platelets and red cells. White cells were plated at $10^6$ cells per 150 mm diameter petri dishes in a solution containing RPMI media, 5 ug/ml of PHA (P-L Biochemicals, Milwaukee, Wis.) and 1.25 mg/ml of human serum. Cultures were incubated for 4 days at 37° C. in a 5% $CO_2$ atmosphere, the supernatant harvested, clarified by centrifugation to remove cell debris, and concentrated approximately 100 fold in a Pellicon hollow fiber concentrator (Millipore, Worthington, NJ). The resulting product is referred to herein as "crude concentrated gamma-interferon".

2. Partial Purification

Crude concentrated gamma-interferon (approximately 500,000 u/ml, 100 mg/ml protein) was passed over a silicic acid (Sigma, St. Louis, Mo.) column which was washed extensively with 1XPBS (0.15M NaCl, 20 mM sodium phosphate, pH 7.2). Gamma-interferon was eluted from this column with 40% ethylene glycol (Fisher Scientific), 1.5M NaCl and 20 mM Sodium Phosphate, pH 7.2. The specific activity of the eluted material was approximately $2\times10^4$ u/mg. Eluted material was dialyzed 4 logs against 1XPBS, aliquoted and stored frozen at $-70°$ C.

3. Anti-Viral Assays

Gamma-interferon anti-viral activity was measured in a cytopathic effect reduction assay using HEp-2 cells and VSV as the challenge virus. Unknown sample titers were calculated and corrected to in-house standards.

4. Acid Inactivation

A. Method 1

Partially purified gamma-interferon prepared as described above (specific activity approx. $2\times10^4$ u/mg) was acidified to a final pH of 2.4 by 1:100 dilution with a citric acid buffer (CAB) composed of 0.3M NaCl and 0.1M citric acid. The temperature of all solutions was kept at 4° C. and mixing of components was done on ice. After acidification, the interferon-containing solutions were incubated at 4° C. for the times indicated below.

B. Method 2

Partially purified gamma-interferon prepared as described above (specific activity approx. $2\times10^4$ u/mg) was acidified to a pH of 2.1 by addition of 10N HCl. The temperature of all solutions was kept at 4° C. and mixing of components was done on ice. After acidification, interferon containing solutions were incubated at 4° C. for the times indicated below.

5. pH Adjustment of the Acidified Solutions

After acid incubation, the pH of the interferon containing solutions were adjusted with either 10N NaOH, solid TRIS, or assay media to a variety of final pHs. Solutions were kept on ice during pH adjustment and swirled gently after adding base. Standard assay media consisted of RPMI (Gibco) supplemented with L-glutamine, amino acids, vitamins, sodium bicarbonate and newborn calf serum to approximately 1 mg/ml.

6. Incubation of the pH Adjusted Solutions

After adjustment of pH, the solutions were sterile filtered, placed at 4° C., and held at that temperature for the times given below.

RESULTS

Acid Deactivation and the Inability of Incubation For a Short Term at an Elevated pH to Restore Substantial Activity As discussed above, it is well known that the activity of gamma-interferon is rapidly reduced to about 10% of its initial value by acid treatment. This effect and the failure of short term incubation at an elevated pH to restore substantial activity is illustrated by the data in Table 1.

In experiments 1-4, a solution containing gamma-interferon was diluted 100 fold into citric acid buffer (final pH 2.4), incubated for 60 minutes on ice, and then pH adjusted to the elevated values shown in Table 1 using 10N NaOH or solid TRIS. At 2 hours after pH adjustment and incubation at 4° C., activities ranged from a high of 21.3% to a low of 8.2% of a control that was prepared by diluting another sample of gamma-interferon 100 fold in assay media (50 mM sodium bicarbonate buffer, pH 7.2) and incubating at 4° C. for 2 hours.

In experiments 5-8, samples prepared in the same manner as the samples of experiments 1-4 (final pH 2.4)

were stored for 8 days at 4° C. and then pH adjusted with NaOH or TRIS. Again, the activity measured after short term incubation (3 hours) at an elevated pH was low (6.3%–13.6%) in comparison with the activity of a control (see above) stored under the same conditions.

In experiment 9, a CAB treated sample showed 21% of control activity after adjustment of its pH to 8.2 with TRIS and incubation at 4° C. for 4 hours. In experiment 10, gamma-interferon, which had been acid treated with 10N HCl (final pH 2.1), recovered 32% of its activity after pH adjustment by 100 fold dilution into assay media and incubation for 4 hours at 4° C.

The gamma-interferon preparation used in the foregoing experiments was found to be completely neutralized by anti-gamma-interferon antisera, but not neutralized by anti-alpha-interferon or anti-beta-interferon antisera. Therefore, all antiviral activity in these experiments is attributable to gamma-interferon only.

Complete Reactivation of Acid Inactivated Gamma-Interferon by Long Term Incubation at an Elevated pH Gamma-interferon was acid inactivated by diluting a 1 ml sample 100 fold in CAB (final pH 2.4) and incubating the sample for 60 minutes on ice. At the same time, a control 1 ml sample was diluted 100 fold in assay media (pH 7.2) and similarly incubated on ice.

The acidified sample was divided into 4 equal aliquots and pH adjustment made with either 10N NaOH (pH 6.9 sample) or solid TRIS (pH 7.5, 8.25 and 9.1 samples). After two hours of incubation at 4° C., samples were assayed for anti-viral activity (see Table 1, Expts. 1–4, and discussion above). All samples including the control were then sterile filtered and incubated further at 4° C. At periodic intervals, samples were removed for anti-viral assay.

As shown in Table 1 (Expts. 1–4), and as discussed above, activity of the pH adjusted samples expressed as a percent of control was low (8.2–21.3%) after 2 hours incubation at 4° C. However, as shown in FIG. 1, nearly complete recovery of activity was achieved after 4 days of incubation at 4° C., irregardless of the final adjusted pH of the solution. After 1 day at 4° C., three of the four samples had activities around 60% of the control activity. By four days after pH adjustment, all samples had around 100% of control activity.

Figure 2:
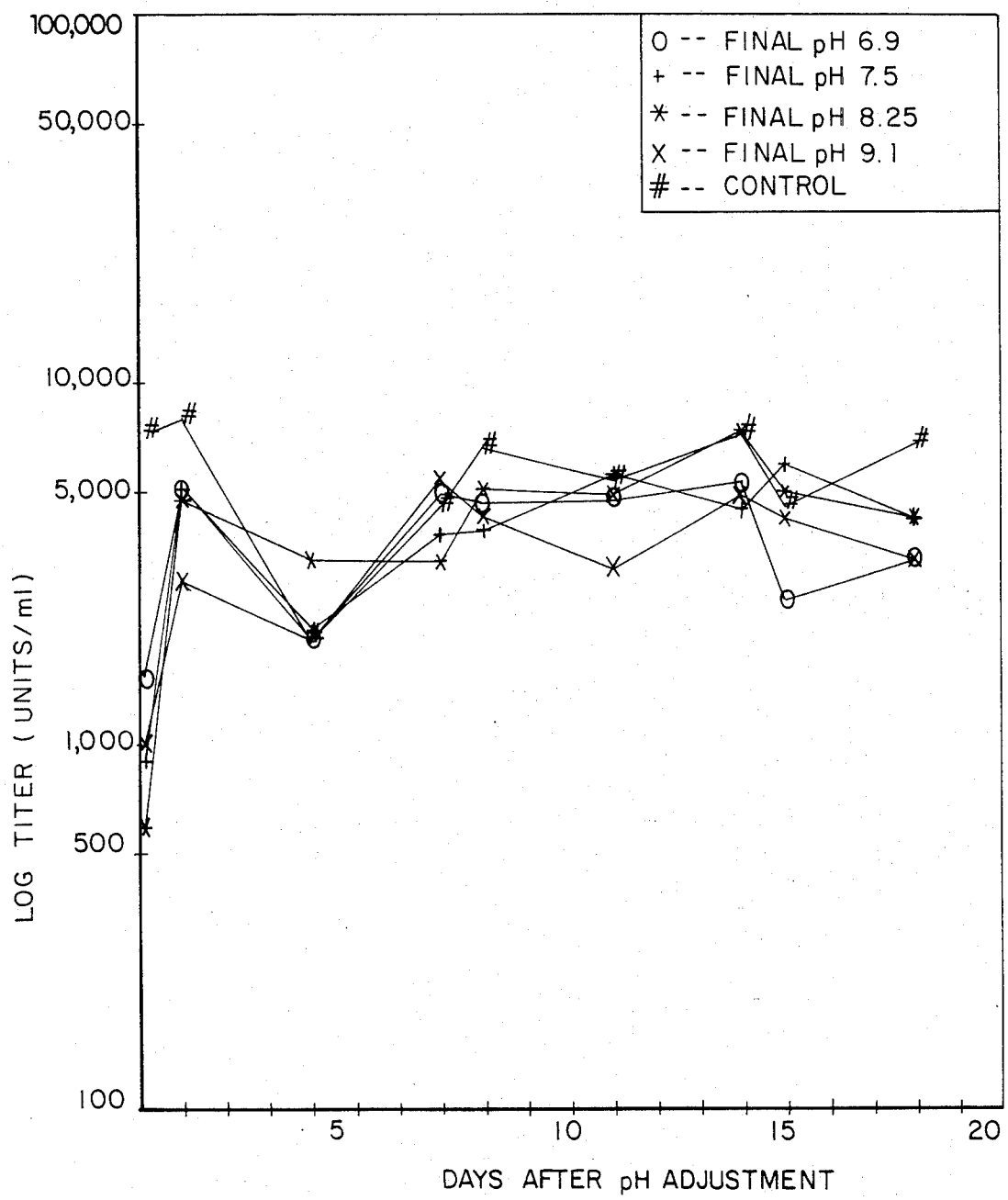
FIG. 2 is a graph showing the absolute titers of the solutions described in FIG. 1. Control data points (#); remaining data points as in FIG. 1.

As shown in FIG. 2, the titers of all acid-treated samples increased after the initial time point (2 hours) and in addition, the titer of the control sample remained fairly constant over the time course of the experiment. This demonstrates that a real reactivation occurred as opposed to there being a relatively constant low level of activity in acid-treated samples combined with a gradual decay in activity of the control sample.

Figure 3:
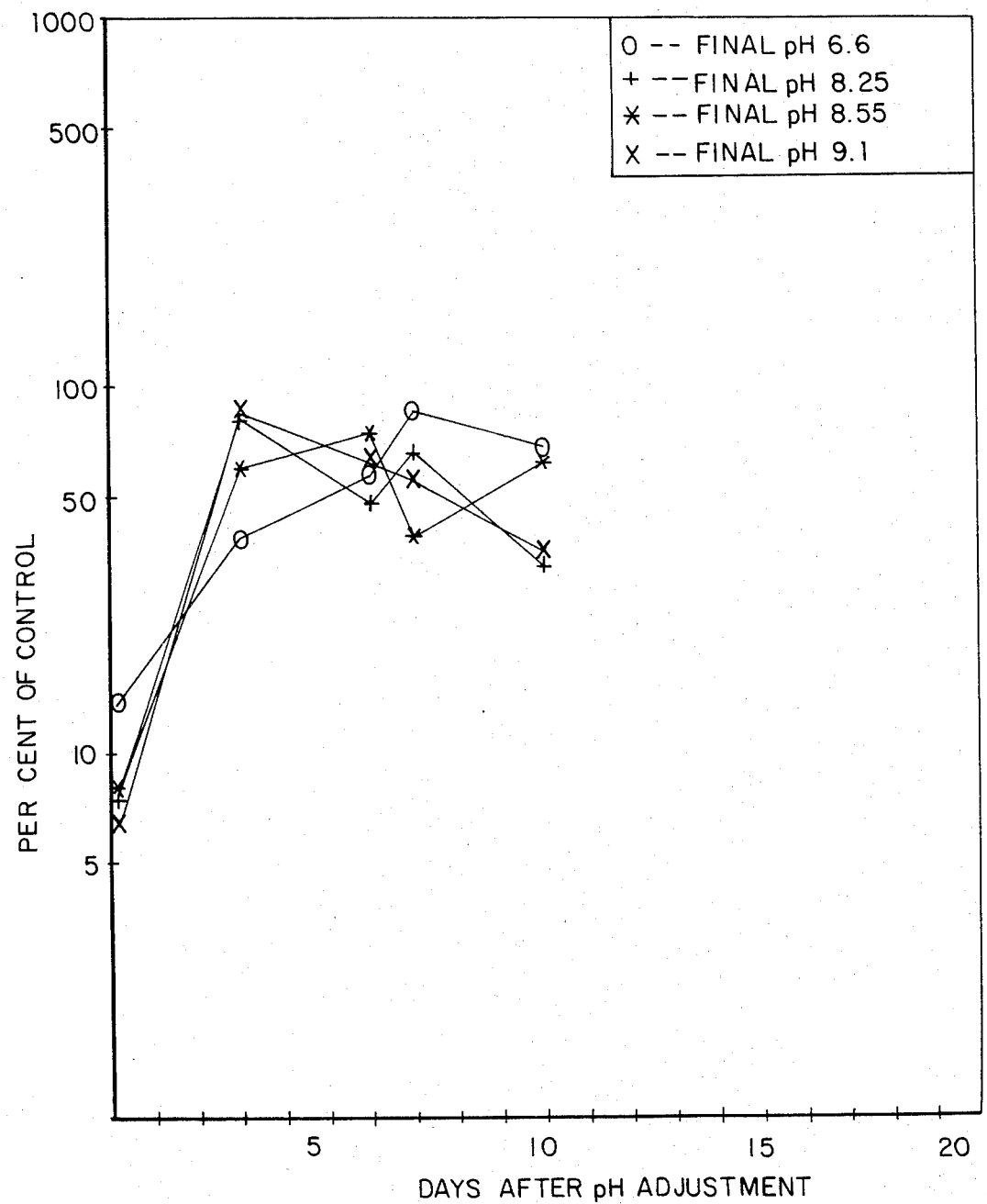
FIG. 3 is a graph showing reactivation of human gamma-interferon incubated at pH 2.4 for 8 days. More particularly, the original acidified mixture of human gamma-interferon (FIGS. 1 and 2) was incubated at 4° C. for 8 days prior to pH adjustment using: NaOH to pH 6.6 (o); solid TRIS to pH 8.25 (+); solid TRIS to pH 8.55 (*); and solid TRIS to pH 9.1 (x). The control for this experiment was identical to that described above for FIG. 1.
Figure 4:
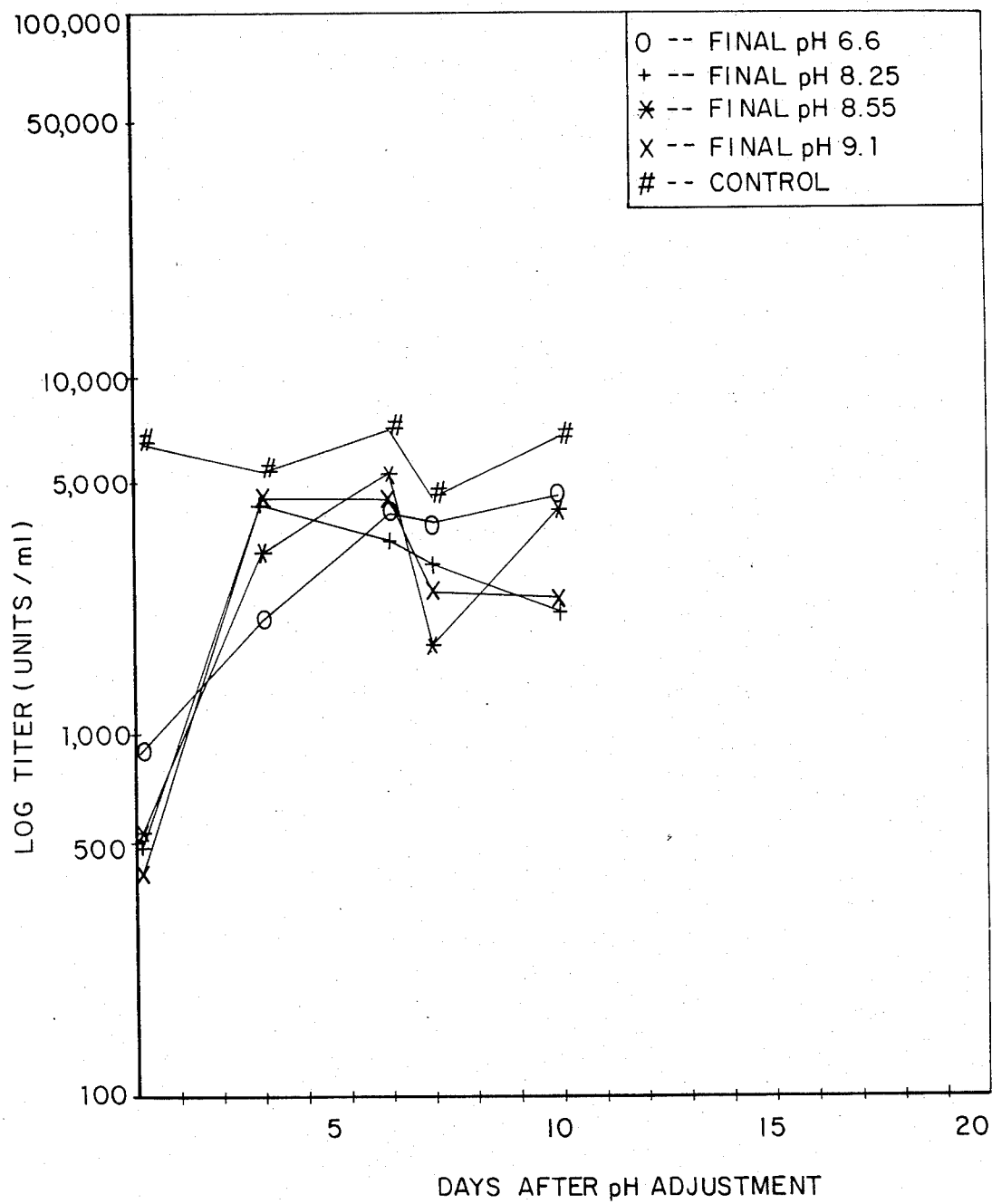
FIG. 4 is a graph showing the absolute titers of the solutions described in FIG. 3. Control data points (#); remaining data points as in FIG. 3.

Similar results were obtained when the same gamma-interferon that was acid treated for 60 minutes (Expts. 1–4 in Table 1) was further incubated for 8 days in CAB at pH 2.4 (Expts. 3–8 in Table 1). As shown in Table 1, three hours after pH adjustment to 6.6, 8.25, 8.55 and 9.1, low levels of activity (6.3–13.6% of control) were observed. However, as shown in FIG. 3, after three days of incubation at 4° C. at elevated pH, two samples (pH 8.25 and pH 9.1) had about 80% of control activity, a third (pH 8.55) had about 60% and the fourth sample (pH 6.6) had about 40% of control activity. Again, titers of acid-treated samples showed an increase from the first time point (3 hours) and the titer of the control sample (identical to that of FIG. 1) remained fairly constant over the course of the experiment (see FIG. 4).

In the two sets of experiments described in FIGS. 1–4, acid-treated and pH adjusted samples were uncontrolled for protein concentration and ionic strength. In both sets of experiments, the control sample had a final protein concentration of about 1.3 mg/ml whereas the acid-treated samples had a protein concentration of 0.3 mg/ml. The ionic strength of the control sample in these experiments is close to physiological saline (approx. 0.15) whereas that of the acid-treated samples was higher since the CAB diluent contains 0.3M NaCl and 0.1M citric acid and the pH adjustment added either TRIS base to about 1M or NaOH to about 0.01M.

To examine the effects of the ionic strength and protein concentration variables on the reactivation process, Experiments 9 and 10 in Table 1 were performed.

In Experiment 9, gamma-interferon was diluted 100 fold in CAB (final pH 2.4), incubated for 60 minutes on ice, and pH adjusted with TRIS to a final pH of 8.2. The control for this experiment was gamma-interferon diluted 100 fold into CAB+TRIS at a pH of 8.2. Accordingly, the protein concentration (0.3 mg/ml), ionic strength ($\cong$0.5), and final pH (8.2) of both the acid-treated and control samples were identical.

Figure 5:
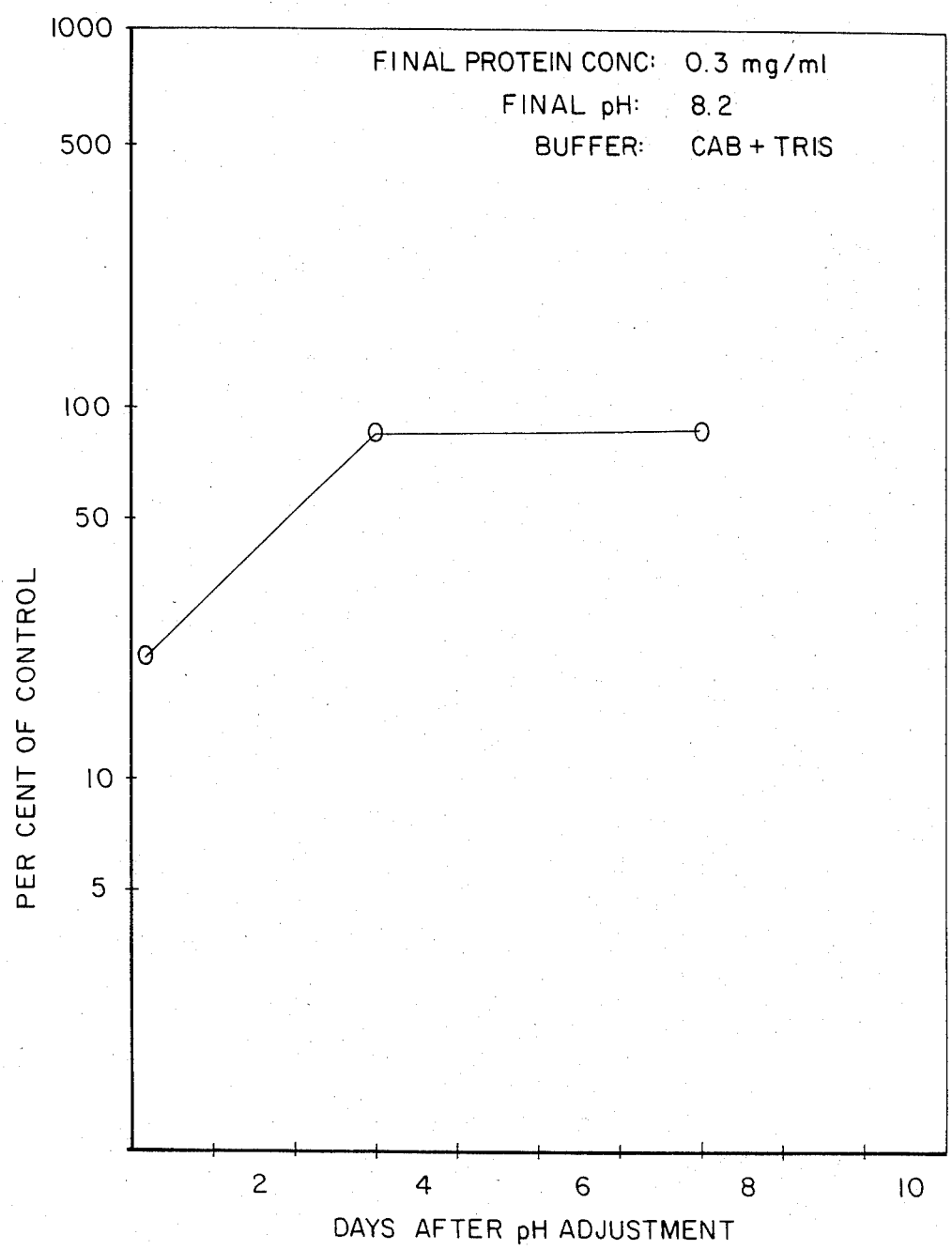
FIGS. 5 and 6 are graphs showing acid inactivation and pH adjustment of gamma-interferon under controlled conditions of total protein concentration, ionic strength, and final pH. More particularly, partially purified gamma-interferon was diluted 1:100 into CAB (pH 2.4), incubated for 60 minutes on ice, and then pH adjusted to 8.2 with solid TRIS (final concentration approximately 1M). This solution was then incubated at 4° C. and titered on days 0 (4 hr.), 3 and 7. The control was diluted 1:100 into CAB+TRIS (approximately 1M), pH 8.2, and incubated at 4° C.
Figure 6:
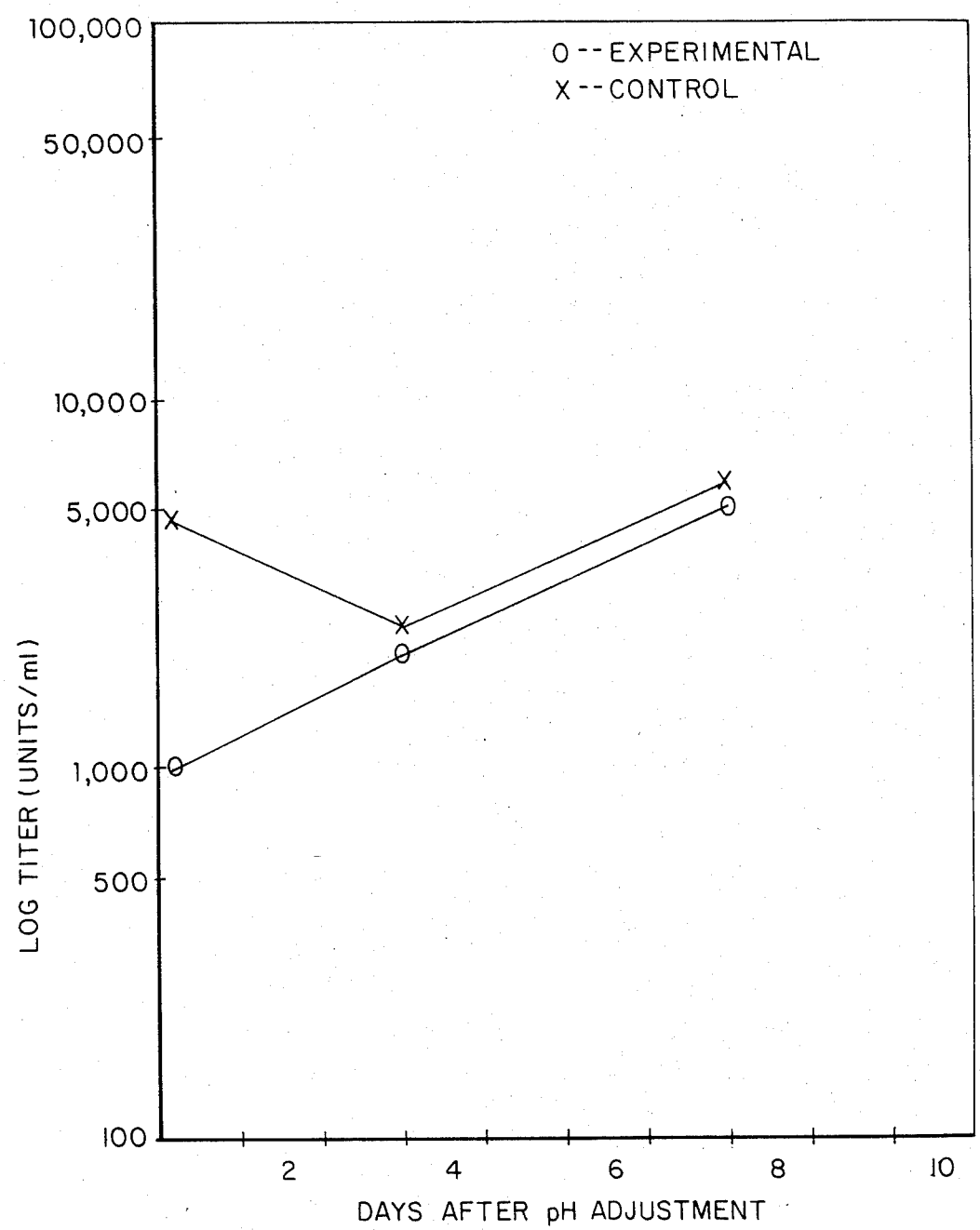

Each sample was incubated at 4° C. for 7 days and assayed at the times shown in FIG. 5. At 4 hours after pH adjustment, the percent activity of the acid-treated sample was 21% of the control. After 3 days of incubation at 4° C., the activity had risen to 84% of the control, and at 7 days, it was 87% of control (FIG. 5). As in previous experiments, the titer of the acid-treated sample increased with time and no decay was apparent in the control sample (FIG. 6).

In Experiment 10 of Table 1, 1 ml of gamma-interferon solution was acidified with 0.010 ml of 10N HCl (final pH 2.1). After 60 minutes incubation on ice, the acidified sample was diluted 100 fold in assay media and incubated at 4° C. The control in this experiment was an identical 1 ml gamma-interferon solution diluted 100 fold in assay media. Again, in this experiment, the protein concentration (1.3 mg/ml), ionic strength ($\cong$0.15) and final pH (7.2) were identical for the sample and the control.

Figure 7:
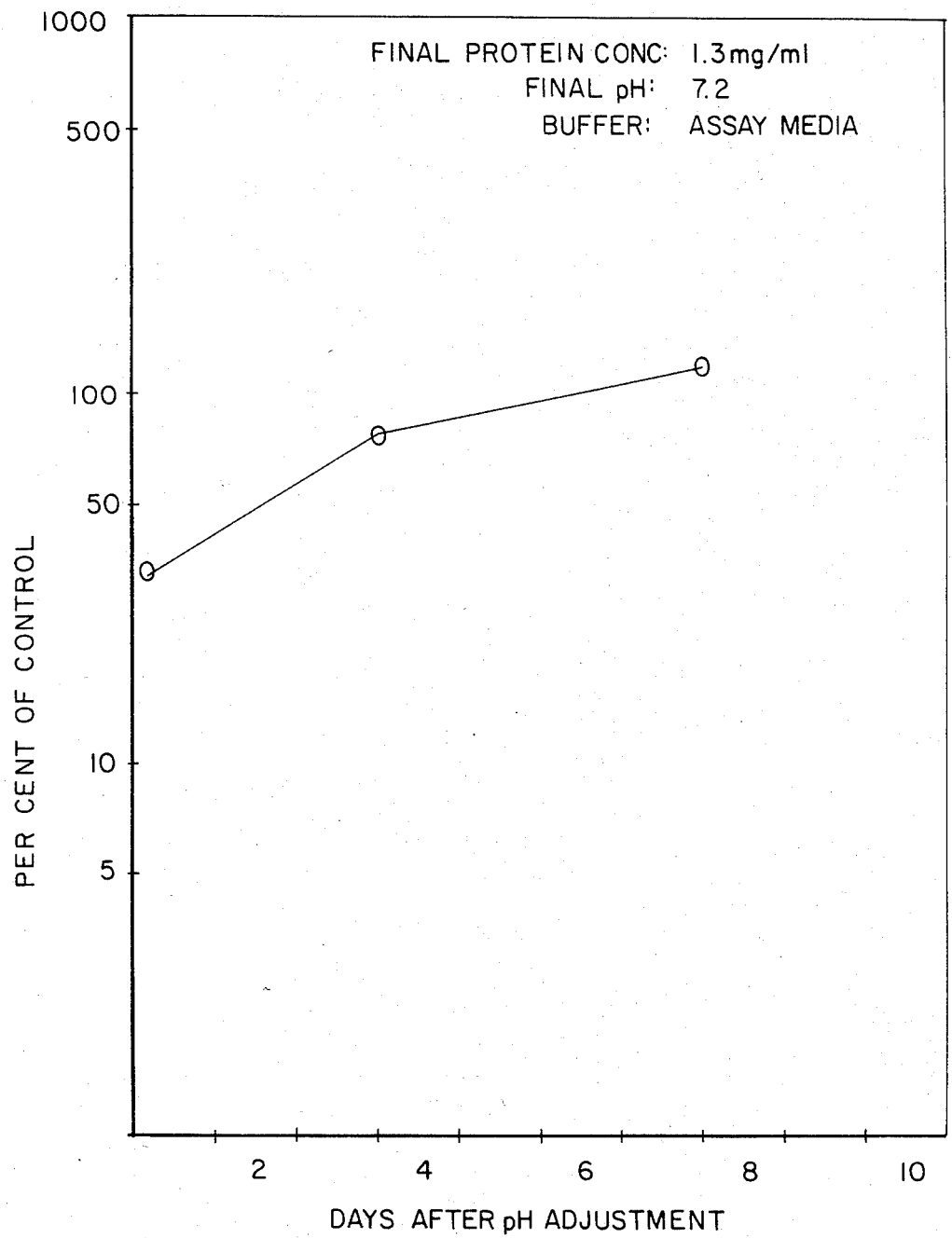
FIGS. 7 and 8 are graphs showing acid inactivation and pH adjustment of gamma-interferon under controlled conditions of total protein concentration, ionic strength, and final pH. More particularly, 1 ml of partially purified gamma-interferon was acidified to pH 2.1 with 0.010 ml of 10N HCl and incubated for 60 minutes on ice. 0.1 ml of this solution was then added to 9.9 ml of assay media. A control sample was incubated on ice for 60 minutes and then 0.1 ml of this sample was added to 9.9 ml of assay media. Both samples were then stored at 4° C. and titered at the times shown in the figure.
Figure 8:
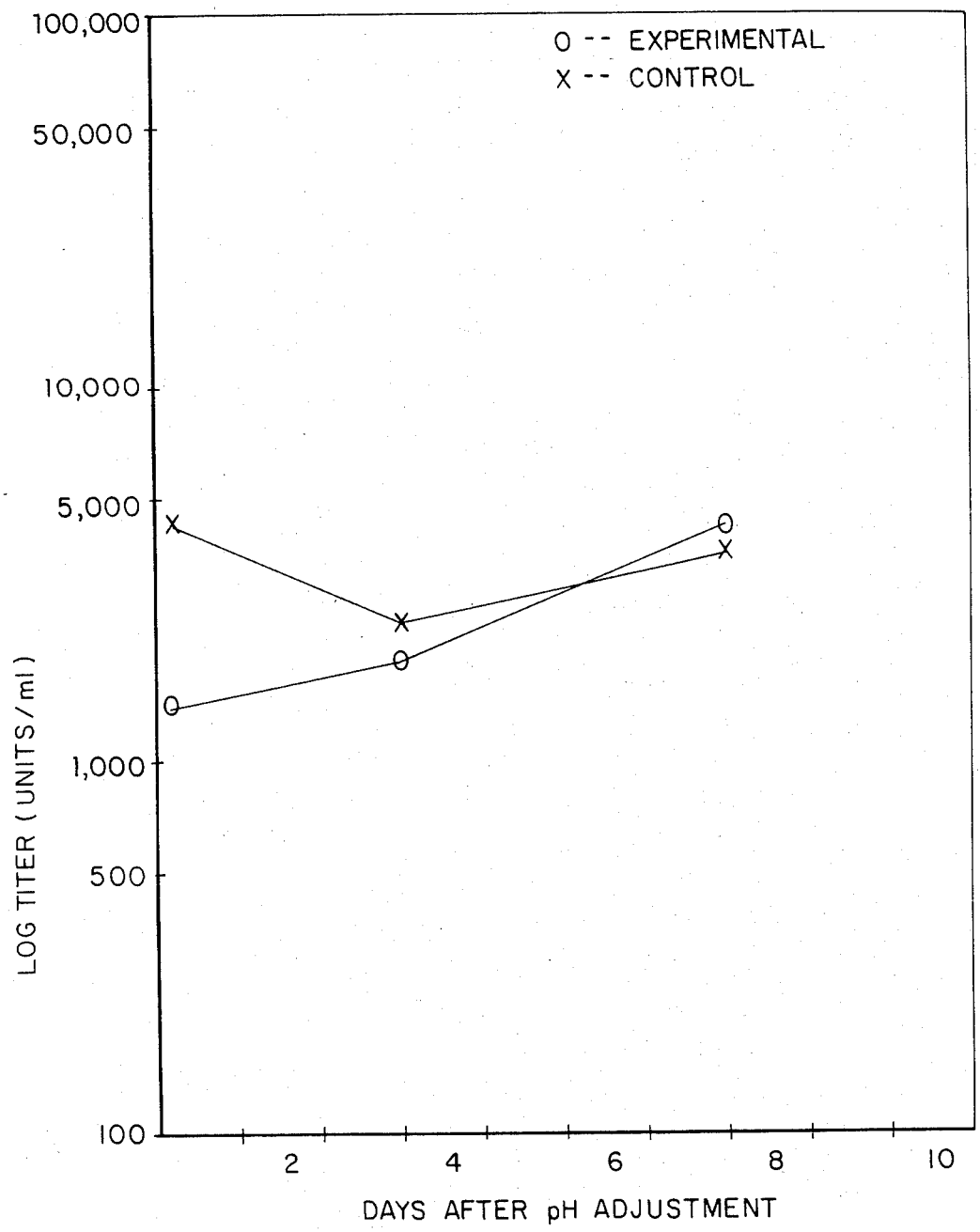

As shown in FIG. 7, at 4 hours after pH adjustment, the activity of the sample was 32% of the control. After 7 days of incubation at 4° C., the pH adjusted sample had regained all of its activity (118%). An increase in titer from the initial time point (4 hours) and a relatively constant control titer were again observed (FIG. 8).

The foregoing data plainly establish that reactivation of acid deactivated gamma-interferon can be accomplished by long term incubation at an elevated pH and a controlled temperature. The reactivation occurs under conditions of both controlled and uncontrolled ionic strength and protein concentration.

TABLE 1

| Acid-Inactivation of Gamma-Interferon | | | | | |
|---|---|---|---|---|---|
| Expt. No. | Acid Used | Solution pH | Duration of Acid Treatment | Adjusted pH | Base Used | % Control Activity |
| 1 | CAB | 2.4 | 60 Min. | 6.90 | NaOH | 21.3 |
| 2 | CAB | 2.4 | 60 Min. | 7.50 | TRIS | 12.5 |
| 3 | CAB | 2.4 | 60 Min. | 8.25 | TRIS | 8.2 |
| 4 | CAB | 2.4 | 60 Min. | 9.10 | TRIS | 13.8 |
| 5 | CAB | 2.4 | 8 Days | 6.60 | NaOH | 13.6 |
| 6 | CAB | 2.4 | 8 Days | 8.25 | TRIS | 7.4 |
| 7 | CAB | 2.4 | 8 Days | 8.55 | TRIS | 8.1 |

TABLE 1-continued

Acid-Inactivation of Gamma-Interferon

| Expt. No. | Acid Used | Solution pH | Duration of Acid Treatment | Adjusted pH | Base Used | % Control Activity |
|---|---|---|---|---|---|---|
| 8 | CAB | 2.4 | 8 Days | 9.10 | TRIS | 6.3 |
| 9 | CAB | 2.4 | 60 Min | 8.20 | TRIS | 21.0 |
| 10 | HCL | 2.1 | 60 Min. | 7.20 | $Na_2CO_3$ | 32.0 |

EXAMPLE 2

Purification of Gamma-Interferon Using Polyclonal Antibodies

A polyclonal antibody column to purify gamma-interferon was constructed in the following manner:

1. Affinity-purified rabbit anti-gamma-interferon IgG available from Interferon Sciences, Inc., (New Brunswick, NJ, Catalog No. 3710) was chromatographed on a protein-Sepharose column that contained the major contaminants, e.g. hemoglobin, IgG, and the like, normally found in the crude product produced by the gamma-interferon production method disclosed in U.S. patent application Ser. No. 446,160, described above. By this procedure, antibodies to the contaminants were absorbed to the column, while antibodies to gamma-interferon passed through the column. At least three chromatography cycles were performed so as to remove as much of the non-anti-gamma-interferon antibodies as possible.

2. The isolated anti-gamma-interferon antibodies obtained by step 1 were coupled to a cyanogen bromide activated Sepharose 4B gel (Pharmacia, Piscataway, NJ) at a concentration of 10 mg of antibody per ml of gel by overnight incubation of the antibodies with the gel in a 0.5M sodium carbonate buffer (pH 8.0).

The column obtained by the above steps was used to purify gamma-interferon in the following manner:

1. Ice-cold sterile filtered crude concentrated gamma-interferon, prepared as described in Example 1, was loaded onto the antibody column at 4° C. using a flow rate of 1 ml/min.

2. After loading, the column was washed extensively with 1x PBS until the column effluent had A280 reading of ≦0.01.

3. Gamma-interferon was then eluted from the column using an ice-cold citric acid buffer (0.1M citric acid, 0.3M NaCl, pH 2.0).

4. Solid Tris (Bio-Rad, Richmond, CA) was added to the ice-cold elution fraction obtained by step 3 until a pH of 9.0 was obtained.

5. The pH-adjusted elution fraction was then sterile filtered and placed at 4° C. to allow reactivation to occur.

The gamma-interferon activities found in the various fractions produced by the above procedure for a typical experiment are shown in Table 2. In order to completely saturate the gamma-interferon binding sites on the column, a large excess of gamma-interferon ($400 \times 10^6$ units) was initially loaded onto the column. The flowthrough material ($300 \times 10^6$ units) was saved and used as load material for subsequent experiments.

The total recovery of units in this experiment was 94% and a specific activity of $\geq 5 \times 10^6$ units/mg was achieved for the elution fraction. This represents a 1000 fold purification of the crude concentrated gamma-interferon applied to the column.

TABLE 2

Purification of Gamma-Interferon On a Polyclonal Antibody Column

| Fraction | Total Units | Specific Activity |
|---|---|---|
| Load | 401 Mu | $5 \times 10^3$ u/mg |
| Flowthrough | 308 Mu | $5 \times 10^3$ u/mg |
| Wash | 13 Mu | — |
| Elution | 55 Mu | $\geq 5 \times 10^6$ u/mg |

That the activity seen in the elution fraction represents gamma-interferon activity, as opposed to alpha-interferon or beta-interferon activity, was established through the use of antibodies specific to alpha, beta and gamma interferon. In accordance with this analysis, the activity of the elution fraction was found to not be neutralized by either an anti-alpha-interferon antibody produced by Interferon Sciences, Inc., (New Brunswick, N.J., Catalog No. 1750) or by an anti-gamma-interferon antibody produced by Cetus Corporation (Emeryville, CA), but was completely neutralized by monoclonal anti-gamma-interferon antibodies produced by both Interferon Sciences, Inc., (Catalog No. 3800) and the Sloan-Kettering Institute, New York, NY (see B. Y. Rubin et al., *Journal of Immunology*, Vol. 130, page 1019, 1983).

To demonstrate the physical and chemical purity of the gamma-interferon eluted from the polyclonal antibody column, a Western blot analysis (see Burnette, W. N., *Anal. Biochem.*, 112:195 (1981)) was performed using the following procedures. First, two samples of the elution fraction were SDS treated and electrophoresed in parallel with four samples of molecular weight marker proteins on a 10–20% polyacrylamide gel gradient (the elution samples were in lanes 2 and 5; the marker proteins in lanes 1, 3, 4, and 6; lanes 1, 2 and 3 were equivalent to lanes 4, 5 and 6, respectively). The electrophoresed samples were next electrophoretically transferred to a sheet of nitrocellulose (see Towbin, H., Stehelin, T., and Gordon, *J. PNAS*, 76:4350 (1979)). Protein bands on the sheet of nitrocellulose were visualized by an immunological staining technique (see De-Blas, A. L., Cherwinski, H. M., *Anal. Biochem.*, 133:214 (1983)) as follows:

(1) The sheet of nitrocellulose was cut in half and part A, containing lanes 1, 2, and 3, was incubated overnight with a mouse monoclonal antibody produced by Interferon Sciences, Inc., (Catalog No. 3800) that specifically recognizes gamma-interferon.

(2) The second half of the sheet of nitrocellulose, part B, containing lanes 4, 5, and 6, was incubated overnight in a control buffer solution without monoclonal antibody.

(3) Both halves of the sheet of nitrocellulose were then incubated with goat anti-mouse polyclonal antibody (Cappel Laboratories, Cochranville, PA).

(4) Both halves were next incubated with a molecular complex consisting of the enzyme peroxidase and mouse monoclonal anti-peroxidase (PAP) (Sternberger-Meyer, Jarretsville, MD).

(5) Finally, both halves were incubated with hydrogen peroxide and 3,3'-diaminobenzidine (DAB) resulting in the appearance of black colored bands on the nitrocellulose.

In view of this procedure, bands appearing in part A, lane 2, and not in part B, lane 5, represent gamma-interferon specific bands, while bands appearing in both lanes 2 and 5 are non-gamma-interferon specific.

Figure 9:
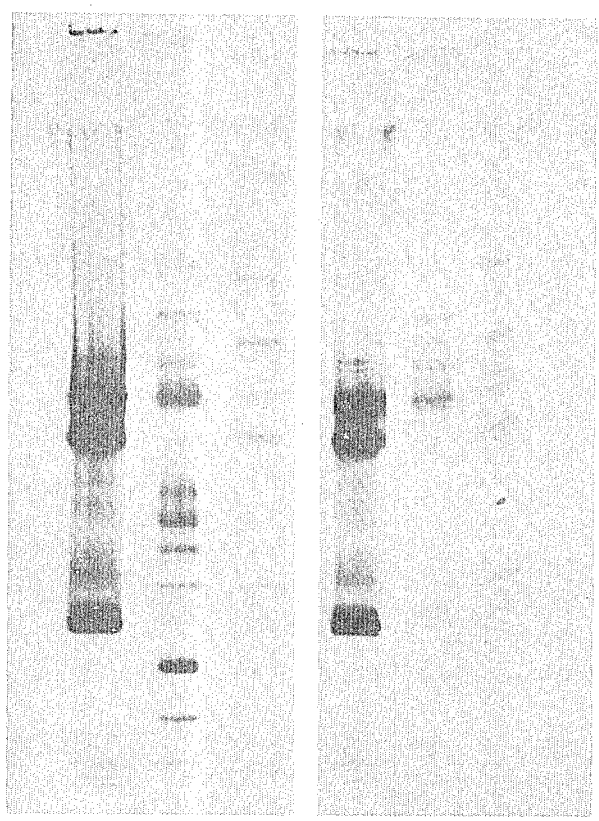
FIG. 9 is a Western blot analysis of the elution fraction from a polyclonal antibody column used to purify gamma-interferon.

The results for the elution fraction obtained as described above are shown in FIG. 9. As can be seen in this figure, gamma-interferon specific bands appear at molecular weight positions 15.5K, 17K, 21K, 30K, 32K, 34K, and 38K daltons. Based on the number of gamma-interferon specific bands relative to the total number of bands in lane 2 of FIG. 9, and assuming that the theoretical specific activity of gamma-interferon is about $1 \times 10^7$ u/mg (see P. Anderson et al, *Journal of Biological Chemistry*, Vol. 258, pages 6497-6502. 1983), these data indicate that the gamma-interferon obtained by chromatography on the polyclonal antibody column was about 50% pure.

EXAMPLE 3

Production of a Monoclonal Antibody To Gamma-Interferon

A monoclonal antibody to human gamma-interferon was obtained as follows.

First, a Balb/c mouse was immunized IP four times at weekly intervals with 0.2 mls of a liposome suspension containing 500 ug of interferon/ml. The mouse received a boost of 100 ug of interferon in incomplete Freund's adjuvant six months after the final liposome injection, then rested for an additional 12 months, during which time the anti-interferon titer remained in excess of $5 \times 10^3$ neutralizing units/ml. Finally, the mouse was boosted IP with 25-50 ug of purified gamma-interferon in incomplete Freund's adjuvant. The human gamma-interferon used for these immunizations was obtained in accordance with the procedures described above and had an activity of approximately $1 \times 10^5$ units/mg for the first five injections and $5 \times 10^6$ units/mg for the final injection.

Three days after the final injection, the spleen cells from the mouse were injected IV into four irradiated recipient Balb/c mice. See Fox, P. C., Barenstein, E. H., and Siraganian, R. P., "Enhancing the frequency of antigen-specific hybridomas", *Eur. J. Immunol.*, 11:431-434, 1981. Each mouse received an IP boost of 25-50 ug of gamma-interferon ($5 \times 10^6$ units/mg) in incomplete Freund's adjuvant. Five days later the spleen cells from these mice were used for fusion.

NS-1-503 myeloma cells were fused with splenocytes by 35% PEG 1000. See Gefter, M. L., Margulies, D. H., and Scharff, M. D., "A simple method for Polyethylene Glycol-Promoted Hybridization of Mouse Myeloma Cells", *Somatic Cell Genetics*, 3:231-236 (1977), and Kawamoto, T., Sato, J. D., Le, A., McClure, D. B., and Sato, G. H., "Development of a Serum-Free Medium for Growth of NS-1 Mouse Myeloma Cells and its Applications to the Isolation of NS-2 Hybridomas", *Analytical Biochemistry*, 130:445-453 (1983). Fused cells were plated into 96 well plates. After two to three weeks, positive wells were cloned by limiting dilution.

The specificity of the monoclonal antibody produced by the fused cells was determined by neutralization assay, precipitation assay, Western blotting and affinity chromatography. It was found that this antibody was specific for human gamma-interferon, and did not bind to human alpha or beta interferons. The monoclonal antibody produced by the foregoing procedure is commercially available from Interferon Sciences, Inc., (Catalog No. 3800).

EXAMPLE 4

Purification of Gamma-Interferon Using A Monoclonal Antibody

A monoclonal antibody column to purify gamma-interferon was constructed in the following manner:

(1) The monoclonal antibody to gamma-interferon produced in accordance with Example 3 was purified by affinity chromatography on a column containing sheep anti-mouse IgG (Cappel Laboratories, Cochranville, PA).

(2) The purified monoclonal antibody was coupled to cyanogen bromide activated Sepharose 4B at a concentration of 10 mg of antibody per ml of gel using the techniques described above in connection with Example 2.

The completed column was used to purify gamma-interferon in accordance with the procedures described above in Example 2 for the polyclonal antibody column.

The data for a typical experiment is shown in Table 3. $22 \times 10^6$ units of gamma-interferon were eluted from the column at a specific activity of $\geq 1 \times 10^7$ units/mg. The overall recovery was 62%.

Figure 10:
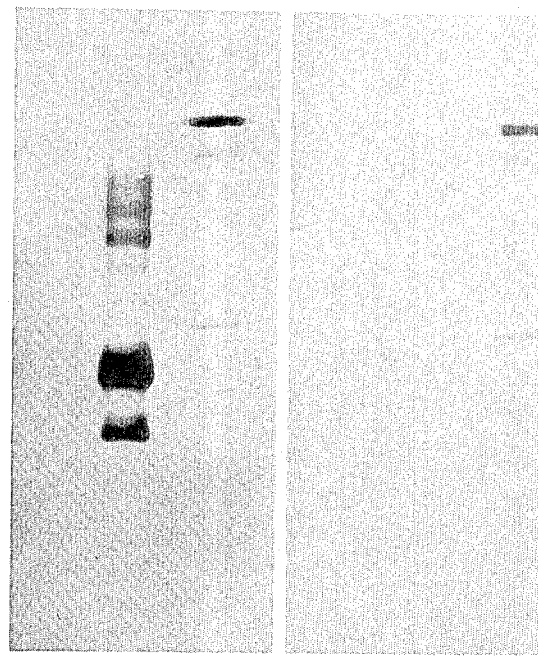
FIG. 10 is a Western blot analysis of the elution fraction from a monoclonal antibody column used to purify gamma-interferon.

FIG. 10 shows the results of a Western blot analysis of the elution fraction obtained from the above column. The procedure used for this analysis was the same as that described above for FIG. 9. Gamma-interferon specific bands (Part A) can be seen at molecular weight positions 15.5K, 17K, 21K, 30K, 32K, 34K, 38K and 40K daltons. The only contaminants appear to be small amounts of mouse IgG heavy chain (50K) which leaked from the column as is commonly observed for antibodies coupled to cyanogen bromide activated Sepharose 4B gels.

The observed specific activity of $\geq 1 \times 10^7$ units/mg and the Western blot analysis together establish that the gamma-interferon eluted from the column was nearly pure.

The results of Examples 2 and 4 plainly show that gamma-interferon of high purity can be removed from antibody columns using acid elution and that nearly full recovery of gamma-interferon activity can be obtained by pH adjustment and incubation under the conditions described in Example 1.

TABLE 3

| Purification of Gamma-Interferon On a Monoclonal Antibody Column | | |
|---|---|---|
| Fraction | Total Units | Specific Activity |
| Load | 87 Mu | $5 \times 10^3$ |
| Flowthrough | 30 Mu | $5 \times 10^3$ |
| Wash | 1.2 Mu | — |
| Elution | 22 Mu | $\geq 1 \times 10^7$ |

Although specific embodiments of the invention have been described and illustrated, it is to be understood that modifications can be made without departing from the invention's spirit and scope. For example, other basic materials in addition to those illustrated can be used to adjust the pH of the interferon-containing solution. Similarly, a variety of chromatography columns and antibody preparations, other than those illustrated, can be used in the practice of this invention.

What is claimed is:

1. A method for purifying gamma-interferon comprising the steps of:

(a) preparing one or more antibodies to gamma-interferon;
(b) immobilizing the one or more antibodies on a solid support;
(c) contacting a first solution containing gamma-interferon with the one or more immobilized antibodies so as to form immobilized antibody-antigen complexes between the gamma-interferon and the one or more immobilized antibodies;
(d) separating the first solution from the immobilized antibody-antigen complexes;
(e) contacting the immobilized antibody-antigen complexes with a second solution having an acidic pH so as to disassociate the gamma-interferon from the one or more immobilized antibodies and into the second solution, the acidity of said second solution having the effect of partially or completely deactivating the diassociated gamma-interferon;
(f) separating the second solution from the one or more immobilized antibodies; and
(g) restoring some or all of the activity of the gamma-interferon in the second solution by adjusting the pH of that solution to between about 5.5 and 9.5 and then incubating the pH adjusted solution at a temperature of between about 2° C. and 8° C. for a period of at least 24 hours.

2. The method of claim 1 wherein the acidic pH of the second solution is between about 1.5 and 4.0.

3. The method of claim 1 wherein the pH of the second solution is adjusted to between about 6.0 and 9.0.

4. The method of claim 1 wherein the pH adjusted second solution is incubated at a temperature of about 4° C.

5. The method of claim 1 wherein the pH adjusted second solution is stored for a period of between about 24 and 96 hours.

6. The method of claim 5 wherein the pH adjusted second solution is stored for a period of about 96 hours.

7. The method of claim 1 wherein the pH of the second solution is adjusted to between about 6.0 and 9.0 and the solution is then stored at a temperature of about 4° C. for about 96 hours.

8. A method for restoring some or all of the activity of gamma-interferon which has been in contact with an acidic solution comprising the steps of:
(a) placing the gamma-interferon in a solution which has a pH between about 5.5 and 9.5; and
(b) incubating the solution at a temperature of between about 2° C. and 8° C. for a period of at least 24 hours.

9. The method of claim 8 wherein the pH of the solution is between about 6.0 and 9.0.

10. The method of claim 8 wherein the solution is incubated at a temperature of about 4° C.

11. The method of claim 8 wherein the solution is incubated for a period of between about 24 and 96 hours.

12. The method of claim 11 wherein the solution is incubated for a period of about 96 hours.

13. The method of claim 8 wherein the pH of the solution is between about 2° C. and 8° C. and the solution is incubated at a temperature of about 4° C. for about 96 hours.

* * * * *